United States Patent
Hogdahl

(10) Patent No.: US 11,077,250 B2
(45) Date of Patent: Aug. 3, 2021

(54) MEDICAMENT DELIVERY DEVICE

(71) Applicant: Carebay Europe Ltd., Sliema (MT)

(72) Inventor: Stefan Hogdahl, Stockholm (SE)

(73) Assignee: SHL MEDICAL AG, Zug (CH)

( * ) Notice: Subject to any disclaimer, the term of this patent is extended or adjusted under 35 U.S.C. 154(b) by 328 days.

(21) Appl. No.: 15/739,967

(22) PCT Filed: Jun. 27, 2016

(86) PCT No.: PCT/EP2016/064840
§ 371 (c)(1),
(2) Date: Dec. 26, 2017

(87) PCT Pub. No.: WO2017/005518
PCT Pub. Date: Jan. 12, 2017

(65) Prior Publication Data
US 2018/0185583 A1 Jul. 5, 2018

(30) Foreign Application Priority Data
Jul. 3, 2015 (SE) .................................. 1550966-4

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157* (2013.01); *A61M 5/326* (2013.01);
(Continued)

(58) Field of Classification Search
CPC ................ A61M 5/2033; A61M 5/326; A61M 2005/2013; A61M 2005/206;
(Continued)

(56) References Cited

U.S. PATENT DOCUMENTS 8,529,510 B2 9/2013 Giambattista et al.
8,551,054 B2 10/2013 Guillermo
(Continued)

FOREIGN PATENT DOCUMENTS

CH 707216 A2 4/2014
CN 102099069 A 6/2011
(Continued)

OTHER PUBLICATIONS

Search Report issued in Swedish Patent Application No. 1550966-4 dated Feb. 3, 2016.
(Continued)

*Primary Examiner* — Nathan R Price
*Assistant Examiner* — Dung T Ulsh
(74) *Attorney, Agent, or Firm* — McDonnell Boehnen Hulbert & Berghoff LLP

(57) ABSTRACT

The present invention relates to a medicament delivery device comprising a housing (16, 18), arranged to accommodate a medicament container (26); a power unit (64) arranged inside said housing, said power unit comprising a plunger rod (112), a drive spring (114) operably arranged to act on the plunger rod (112) and, which is, upon activation, operably arranged to act on said medicament container (26), an actuator (90) comprising holding elements (94, 100), capable of releasably holding said plunger rod (1112) with said drive spring (114) in a tensioned state, and an actuator sleeve (76) operably connected to said actuator (90) for releasably locking said holding elements (94, 100) in a holding state; said medicament delivery device further comprising a medicament delivery member guard (34) slidably movable in said housing (16, 18) and arranged to act on said actuator sleeve (76) for setting said holding elements (94, 100) with said actuator sleeve (76) in a first activation state; an activator unit (124) arranged to be manually operated
(Continued)

and, which is, operably connected to said plunger rod (112) for setting said holding elements (94, 100) with said actuator sleeve (76) in a second activation state, wherein said plunger rod (112) is released when both activation states are set.

17 Claims, 9 Drawing Sheets

(52) U.S. Cl.
CPC ............... *A61M 2005/206* (2013.01); *A61M 2005/208* (2013.01); *A61M 2005/2013* (2013.01); *A61M 2205/581* (2013.01)

(58) Field of Classification Search
CPC .............. A61M 2005/208; A61M 5/20; A61M 5/31576; A61M 5/31578
See application file for complete search history.

(56) References Cited

U.S. PATENT DOCUMENTS

| | | | |
|---|---|---|---|
| 9,861,754 B2 | 1/2018 | Holmquist | |
| 2005/0101919 A1 | 5/2005 | Brunnberg | |
| 2012/0123350 A1* | 5/2012 | Giambattista | A61M 5/2033 604/198 |
| 2014/0058333 A1* | 2/2014 | Cross | A61M 5/002 604/198 |
| 2015/0273162 A1 | 10/2015 | Holmquist | |
| 2016/0015901 A1 | 1/2016 | Plumptre | |
| 2016/0051765 A1 | 2/2016 | Morris et al. | |
| 2016/0067411 A1 | 3/2016 | Morris | |
| 2016/0367763 A1 | 12/2016 | Tschirren et al. | |
| 2018/0344937 A1 | 12/2018 | Loof et al. | |

FOREIGN PATENT DOCUMENTS

| | | | |
|---|---|---|---|
| JP | 2005-531349 | A | 10/2005 |
| JP | 2012532657 | A | 12/2012 |
| TW | 201417853 | A | 5/2014 |
| TW | 201431577 | A | 8/2014 |
| TW | 201503923 | A | 2/2015 |
| TW | 201509458 | A | 3/2015 |
| TW | 201509467 | A | 3/2015 |
| TW | 201521088 | A | 6/2015 |
| WO | 2011005177 | A1 | 1/2011 |
| WO | 2015131294 | A1 | 9/2015 |

OTHER PUBLICATIONS

Search Report issued in Taiwanese Patent Application No. 105120602 dated Apr. 7, 2017.

First Office Action issued in Japanese Patent Application No. 2017-567423 dated Dec. 4, 2018.

* cited by examiner

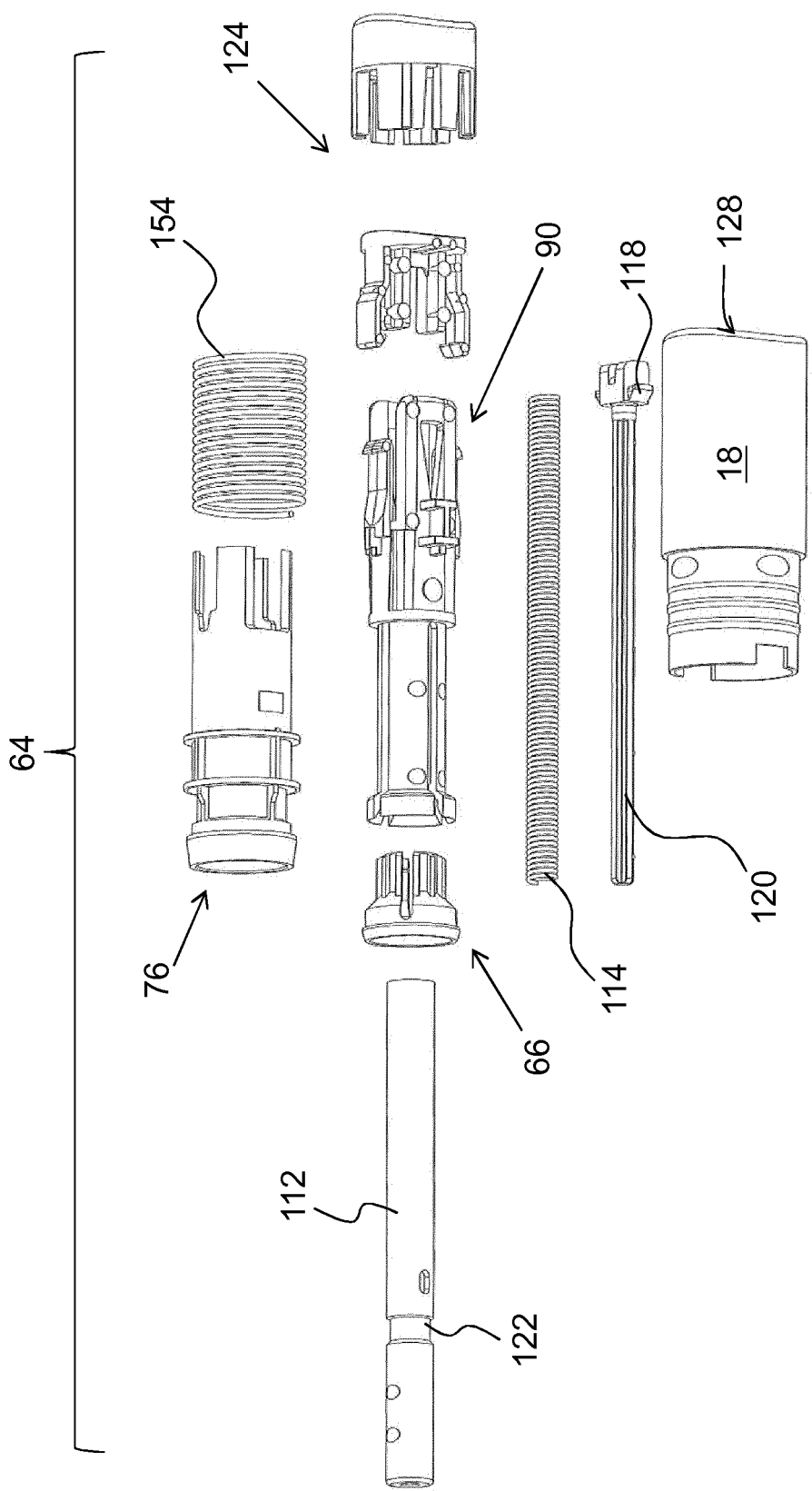

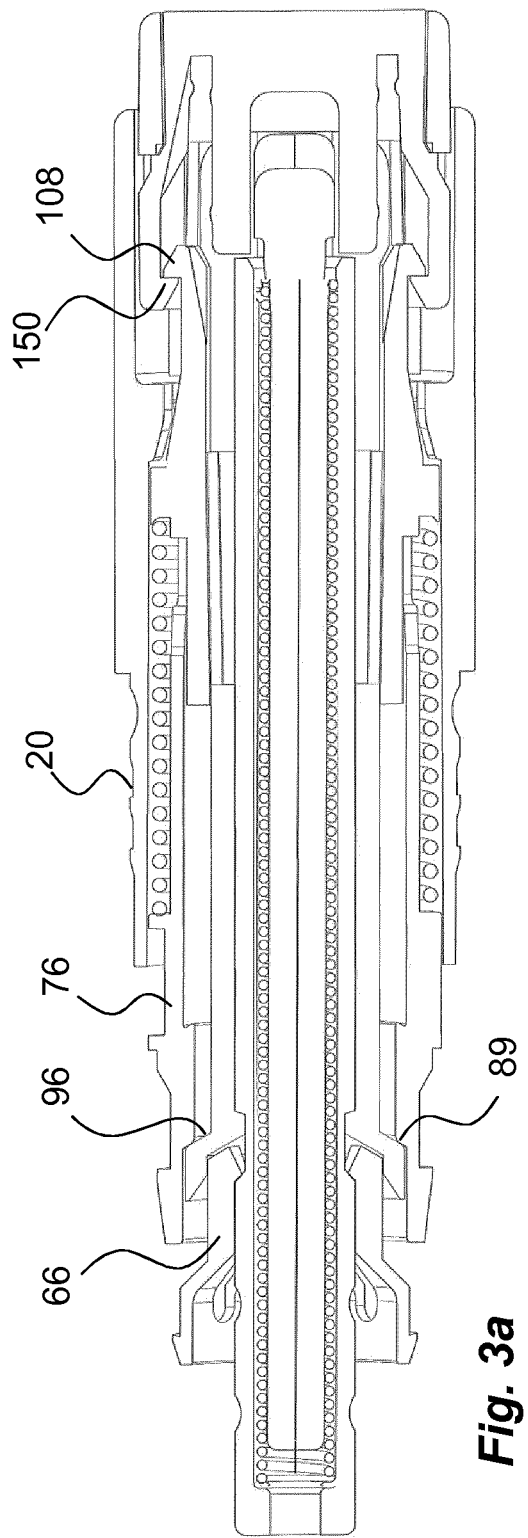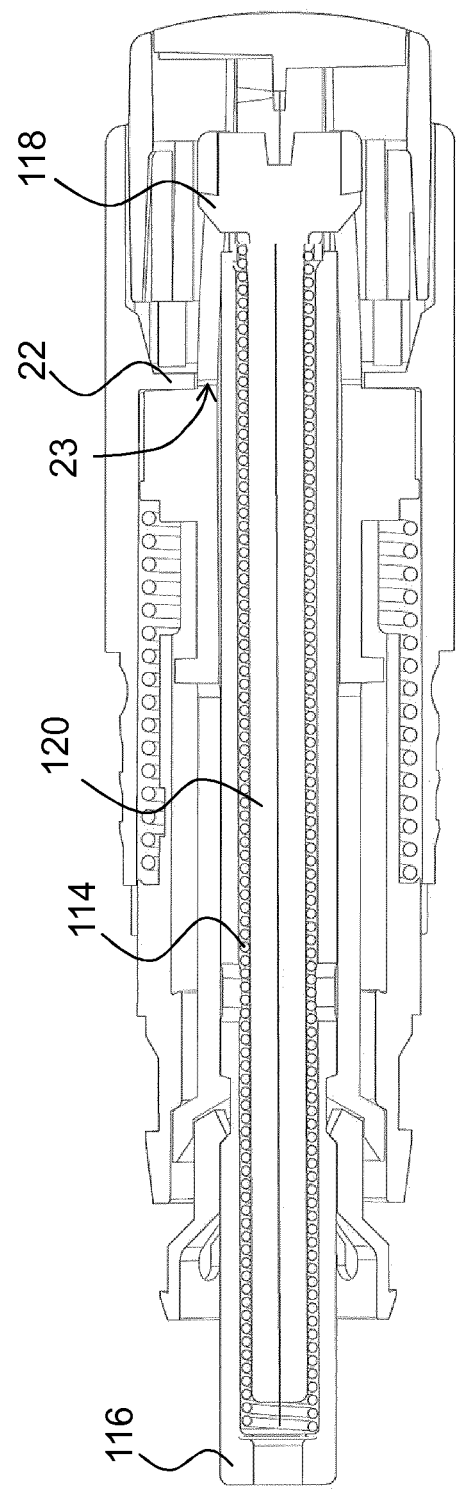
Fig. 3a
Fig. 3b

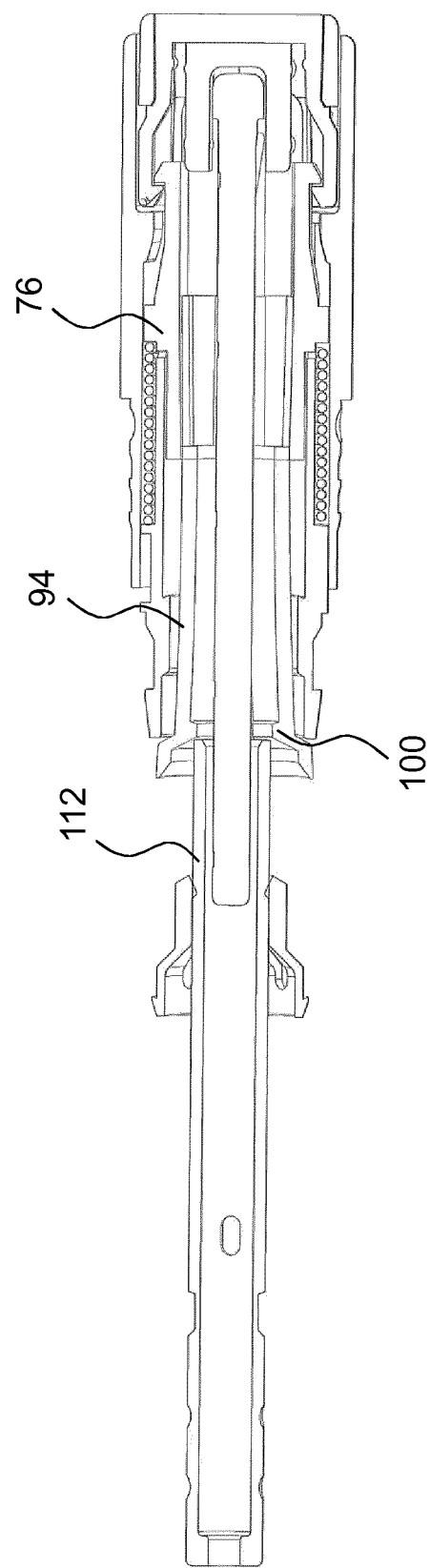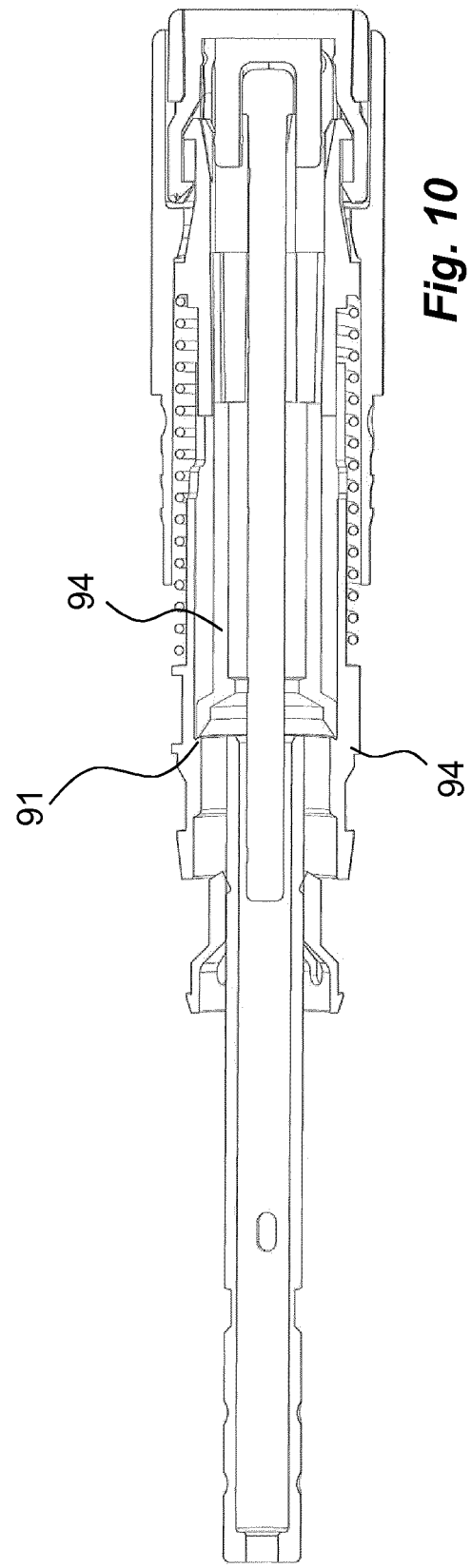

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/064849 filed Jun. 27, 2016, which claims priority to Swedish Patent Application No. 1550966-4 filed Jul. 3, 2015. The entire disclosure contents of these applications are hereby incorporated by reference into the present application.

TECHNICAL AREA

The present invention relates to a medicament delivery device comprising a power unit with a specific activation mechanism.

BACKGROUND OF INVENTION

A large number of medicament delivery devices for self-medication have been developed during the years, where many have a high degree of automatic functions and features in order to facilitate the use of the medicament delivery device, especially for unexperienced users.

One device that has gained a lot of attention on the market for its functionality is disclosed in the document WO 2011/005177 A1. The device disclose therein has a number of automatic features like auto-penetration, auto-injection and automatic covering of the injection needle after removal of the medicament delivery device from the doe delivery site.

Even though working very well, the medicament delivery device according to WO 2011/005177 A1 comprises quite a lot of components that on the one hand provides an increased complexity regarding interaction between the components as well as increased assembly complexity and on the other hand increased manufacturing costs due to the number of components.

In view of this, there is room for further development of the functionality of medicament delivery devices in line with the medicament delivery device disclosed in WO 2011/005177 A1.

BRIEF DESCRIPTION OF INVENTION

The aim of the present invention is to remedy the drawbacks of the state of the art medicament delivery devices and to provide a solution with a good functionality.

The aim is solved by a medicament delivery device comprising the features of the independent patent claim. Preferable embodiments of the invention form the subject of the dependent patent claims.

The medicament delivery device may comprise a housing arranged to accommodate a medicament container. The housing may include a power unit arranged inside said housing. The power unit comprises a plunger rod, a drive spring, an actuator, and an actuator sleeve. The drive spring is operably arranged to act on the plunger rod, and which is, upon activation, operably arranged to act on the medicament container.

Further, the actuator may be arranged with holding elements, capable of releasably holding the plunger rod with the drive spring in a tensioned state. The actuator cooperates with the actuator sleeve operably connected to the actuator for releasably locking the holding elements in a holding state.

According to a favourable solution, the medicament delivery device may further comprise a medicament delivery member guard slidably movable in said housing and arranged to act on the actuator sleeve for setting the holding elements in a first activation state and an activator unit arranged to be manually operated, operably connected to said plunger rod for setting the holding elements in a second activation state, wherein the plunger rod is released when both activation states are set.

Thus both conditions have to be fulfilled in order to activate and release the plunger rod from the tensioned state. There is no sequence dependency, i.e. there is no need to follow a sequence by first setting the first activation state followed by setting the second activation state. An advantage is that a user will not be confused how to activate the device. A further advantage with the solution is that the manually operated activation mechanism is operably connected to the plunger rod, thereby reducing the number of components that are used for activating the medicament delivery device.

According to one favourable solution, the holding elements may comprise a number of arms arranged with ledges arranged to engage recesses in plunger rod, thereby providing a positive mechanical locking function. in this respect, the actuator sleeve may be arranged slidable in relation to the actuator, wherein movement of the medicament delivery member guard in a distal direction causes the actuator sleeve to move distally to the first activation state. Thus the actuator sleeve connected to the medicament delivery member guard will cooperate with the actuator for setting the device in the first activation state.

The activator unit may preferably be slidably movable, wherein movement of the activator unit in a proximal direction causes said plunger rod to move to the second activation state. Thus, there are movements in opposite directions for activating the medicament delivery device by setting the medicament delivery device in the two activation states. The activator unit may preferably comprise push elements arranged to act on an end surface of the plunger rod. This enables a design of the activator unit as for example a push button or the like manually operated mechanism.

According to a further preferable solution, the medicament delivery device may further comprise an end-of-dose signal mechanism. With such a mechanism, the user is alerted that the dose has been delivered and that it is safe to remove the medicament delivery device from the dose delivery site.

The end-of-dose signal mechanism may according to one solution comprise the drive spring operably arranged between the plunger rod and the actuator. It may further comprise lock/release elements arranged to releasably locking the actuator until the plunger rod has reached a proximal end position, wherein the lock/release elements releases the actuator, whereby the actuator is urged in the distal direction by the drive spring so that the actuator hits a fixed surface, producing said end-of-dose signal. This will thus produce an audible as well as a tactile signal to the user.

According to a feasible solution, the lock/release elements may comprise the holding elements and wherein said holding elements are arranged in the locking position by the plunger rod. Thus the same components can have multiple functions.

In order to increase the safety of the medicament delivery device, it may further comprise a medicament delivery member guard spring arranged to force the medicament delivery member guard in a proximal direction after removal of the medicament delivery device and in that respect, the medicament delivery device may further comprises a medicament delivery member guard locking mechanism. This ensures that the medicament delivery member guard cannot be pushed distally after removal from the dose delivery site, preventing accidental injuries.

In this respect, the medicament delivery device may further comprise a medicament delivery member guard locking signal mechanism. According to one favourable solution, the medicament delivery member guard locking signal mechanism may comprises the tongues of the holding elements interacting with a ledge on an inner surface of the actuator sleeve such that movement of the medicament delivery member guard in the proximal direction will cause the tongues to pass the ledge and flex in a generally radial direction, thereby causing a medicament delivery member guard locking signal. Thus, the user will then be presented with a second signal indicating that the medicament delivery member guard is safely locked and that the medicament delivery device now may be discarded.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 2 shows an exploded view of a power unit comprised in the medicament delivery device of FIG. 1, FIG. 3 is a cross-sectional view of the power unit of FIG. 2, FIGS. 4-6 are detailed views of components comprised in the power unit of FIG. 2, and FIGS. 7-10 are cross-sectional view showing different functional states of the power unit of FIG. 2.

DETAILED DESCRIPTION OF THE INVENTION

Figure 1:
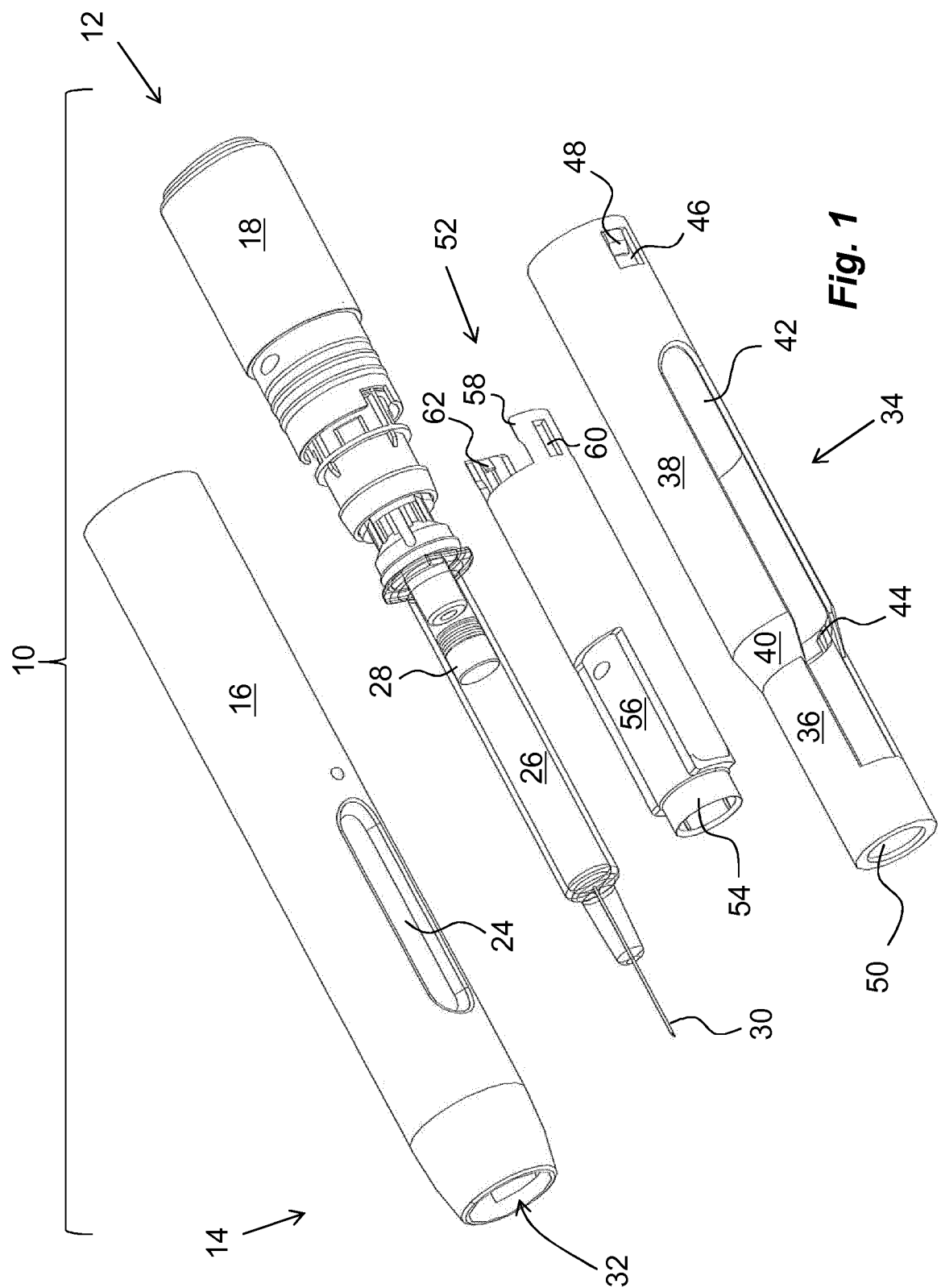
FIG. 1 shows an exploded view of an example of a medicament delivery device.

FIG. 1 shows an example of an embodiment of a generally elongated medicament delivery device 10 comprising the present invention and having a distal end 12 and a proximal end 14. The medicament delivery device is provided with an elongated housing, comprising a proximal housing part 16 and a distal housing part 18. The distal end of the proximal housing part 16 is arranged with engagement means (not shown) such as annular recesses e.g. on its inner surface adapted to interface with corresponding engagement means 20, FIG. 3a, on e.g. the proximal outer surface of the distal housing part 18. The distal housing part 18 is further arranged with a central wall 22, FIG. 3b, which wall 22 is provided with a central passage 23.

The proximal housing part 16 is arranged with elongated openings 24 for viewing a medicament container 26. The medicament container 26 is arranged with a movable stopper 28 and a medicament delivery member 30. In the embodiment shown, the medicament delivery member 30 is integrated in the medicament container 26, but it is to be understood that the medicament delivery member 30 may be an attachable member wherein the attachment elements may be threads, bayonet fittings or luer-couplings, just to mention a few.

The proximal housing part 16 is further arranged with a central passage 32 through which a medicament delivery member guard 34 can extend. The medicament delivery guard 34 comprises a first proximal part 36 having a certain diameter and a second distal part 38 having a diameter larger than the proximal part, where these parts are joined by an intermediate conical part 40, FIG. 1. Two elongated slits 42 are arranged along the medicament delivery member guard 34, on opposite sides thereof, for viewing the medicament container 26. On an inner surface of the conical part 40 a ledge 44 is arranged.

Further, at the distal end of the medicament delivery member guard 34 two openings 46 are arranged opposite each other, where each opening 46 is arranged with somewhat inwardly projecting, flexible, tongues 48, FIG. 1. The medicament delivery member guard 34 is further arranged with a central opening 50 at its proximal end, through which the medicament delivery member 30 may protrude as will be described.

A generally tubular medicament container holder 52 is slidably and coaxially arranged inside the medicament delivery member guard 34. The proximal part of the medicament container holder 52 is arranged with a neck portion 54 of lesser diameter. Adjacent the neck portion 54 cut-outs have been made on either side to form guide surfaces 56. These surfaces 56 cooperate with corresponding shapes of the inner surface of the medicament delivery member guard 34 in order to obtain a stop mechanism against rotation of the medicament container holder 52 relative the medicament delivery member guard 34. The distal end of the medicament container holder 52 is arranged with two distally extending tongues 58, where each tongue is arranged with an opening 60 and an inwardly directed ledge 62 on the distal edge of each opening, FIG. 1.

The present invention relates to a power unit 64, FIGS. 2-5, that may be comprised in the medicament delivery device described above. The power pack comprises a holding element 66. It comprises a ring-shaped body 68, FIG. 4, having an annular ledge 70 arranged around its circumference and a number of flexible tongues 72 directed towards the distal end of the device and wherein each tongue 72 is arranged with radial inwardly directed ledges 74. The holding element 66 is intended to interact with the container holder 52 as will be described below. The power unit 64 further comprises an actuator sleeve 76 which is slidably and coaxially arranged to the housing and connected to the medicament delivery member guard 34 as will be described below.

Figure 4:
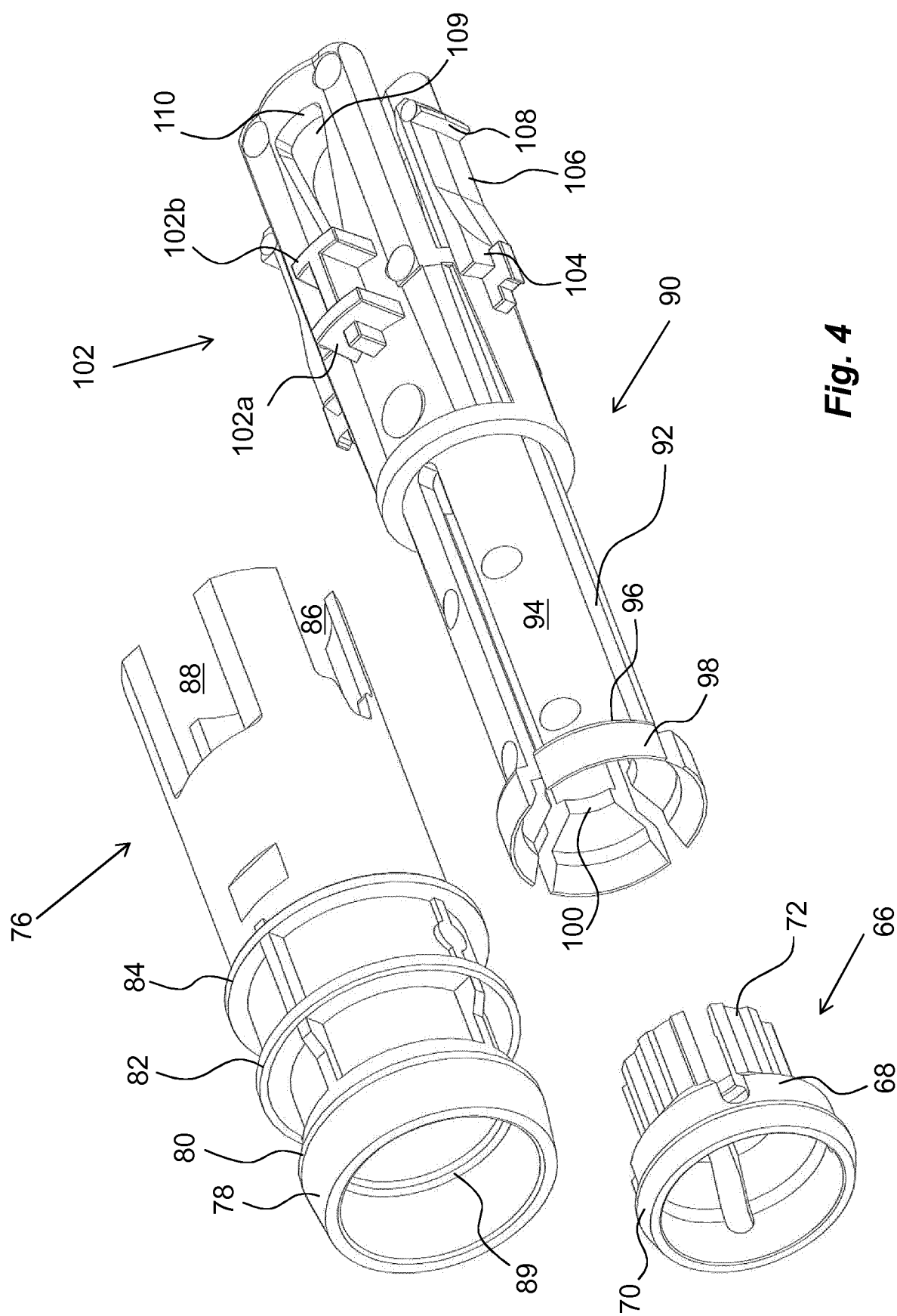
Figure 5:
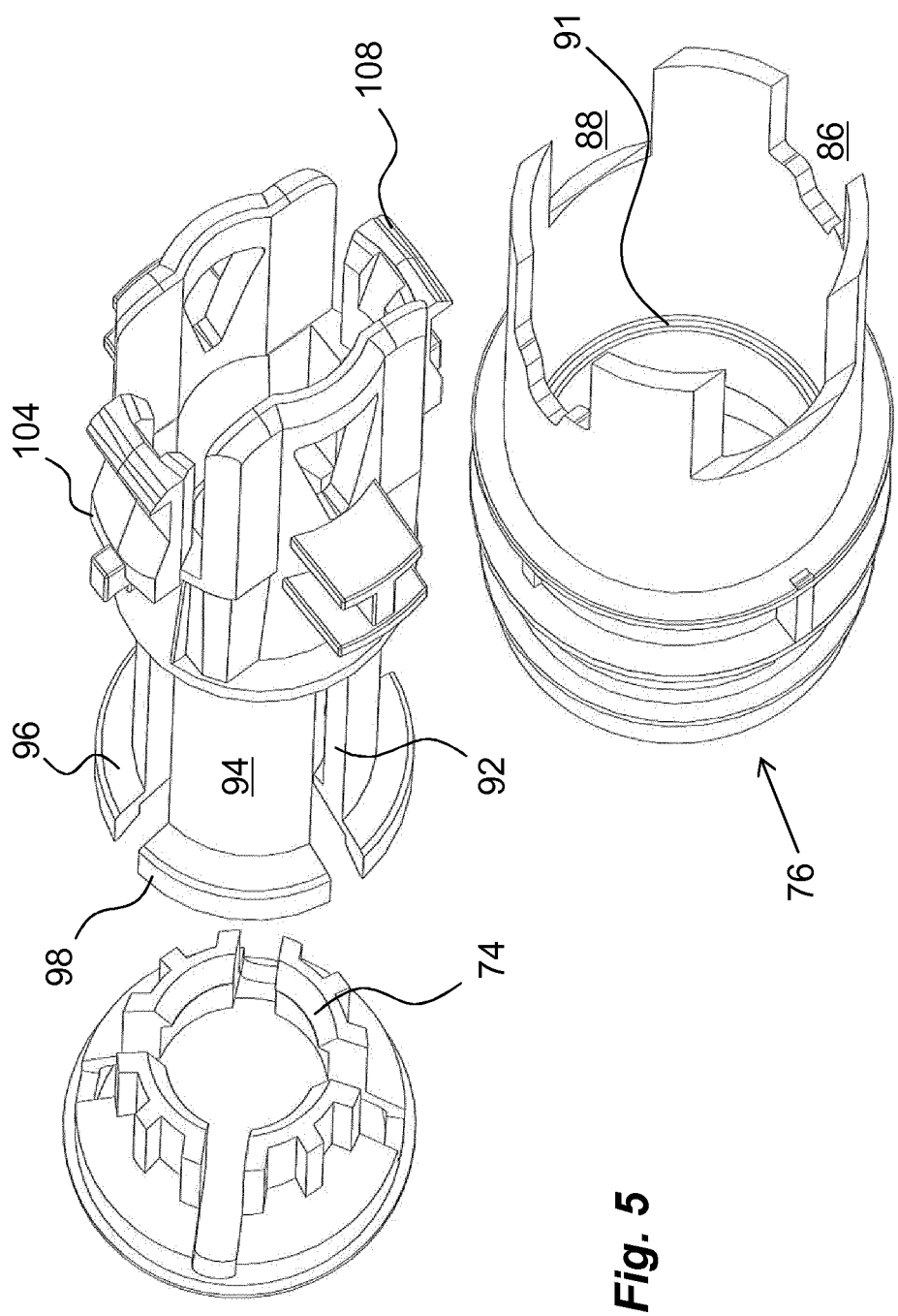

The actuator sleeve 76 has a tubular shape and comprises a proximal end with a conical part 78 ending in a ledge 80 on its outer surface. At a distance from the ledge 80, a first annular ring 82 is arranged on the outer surface. A second annular ring 84 is also arranged a further distance from the ledge 80. The distal end of the actuator sleeve 76 is arranged with at least two oppositely arranged first cut-outs 86 of a generally rectangular shape. The distal end of the actuator sleeve 76 is further arranged with two oppositely arranged second cut-outs 88. An annular, proximally directed, ledge 89, FIG. 4, is arranged on the inner surface of the actuator sleeve 76. The actuator sleeve is further arranged with a distally directed, annular, ledge 91, FIG. 5.

A generally tubular actuator 90 is slidaby and coaxially arranged to the actuator sleeve 76. The actuator comprises a number of longitudinally directed cut-outs 92 that are arranged at the proximal end of the actuator 90 so as to form flexible tongues 94. The proximal end of each flexible tongue 94 has an inclined transition surface 96 which meets with a band-shaped part 98 with enlarged diameter. On the inner surface adjacent the transition surface 96 an annular inwardly directed ledge 100 is arranged. The tongues 94 with the ledges 100 form holding elements as will be described.

The actuator 90 is also provided with two oppositely arranged stop elements 102 directed radially outwards from the outer surface on either side and having a proximally directed ledge 102a, where the widths of said proximally directed ledge 102a correspond to the width of the first cut-outs 86 of the actuator sleeve 76, FIG. 3. The stop elements 102 further has a distally directed ledge 102b, the function of which will be described below. The stop elements 102 are arranged to fit into the second cut-outs 88. The actuator 90 is further provided with at least two oppositely ledges 104 directed radially outwards from the outer surface on either side arranged to mate the first cut-outs 86 of the of the actuator sleeve 76.

Further, the ledges 104 extend in the distal direction and are transformed into generally radially flexible arms 106, where the free ends of the arms are arrange with outwardly directed ledges 108. Further, the distal end of the actuator 90 is arranged with cut-outs 109, which form proximally directed support surfaces 110, the function of which will be described below.

The power unit 64 further comprises a plunger rod 112 arranged to act on the stopper 28 of the medicament container 26. A drive spring that in the embodiment shown is a compression spring 114 is arranged inside the plunger rod 112 between a proximal wall 116 of the plunger rod 112, FIG. 2b, and a proximally directed support surface of generally radially directed ledges 118 arranged in a distal area of an elongated guide rod 120, which is extending through the drive spring 114. The ledges 118 of the guide rod 120 are arranged to fit inside the cut-outs 109 and engage with the support surfaces 110 of the actuator 90. The plunger rod 112 is arranged with a number of recesses that in the embodiment shown is a circumferential groove 122 with a certain width, wherein the annular inwardly directed ledge 100 of the actuator 90 and the radial inwardly directed ledges 74 of the holding element 66 fit into, Fig. It is to be understood that the groove 122 may be replaced with a number of discrete recesses or cut-outs.

Figure 6:
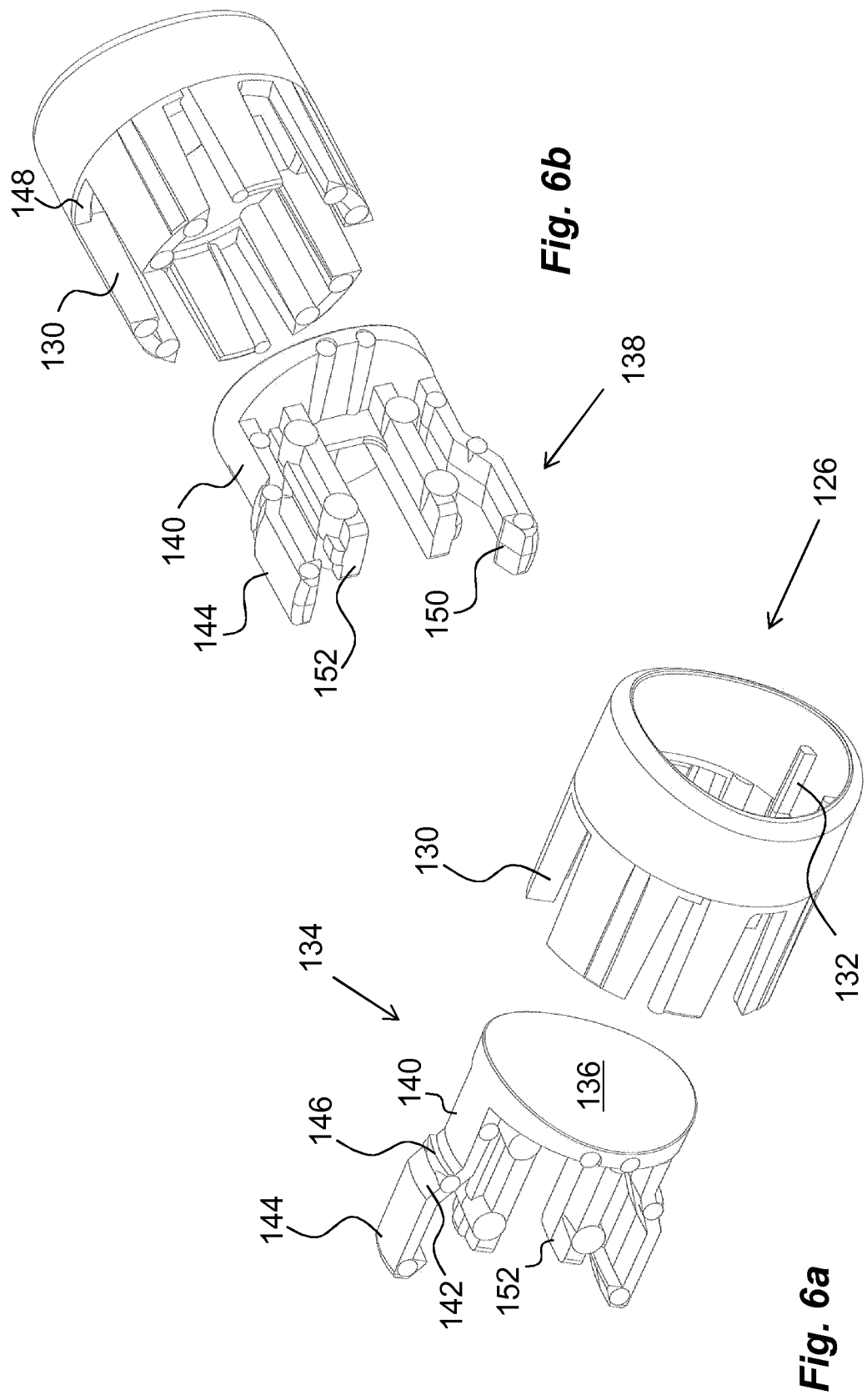

A manually operated activator unit 124, e.g. a push button, has a distal portion protruding distally from the distal housing part 18. The activator unit 124 is arranged with two parts. An outer tubular first part 126, FIG. 6, is arranged slidable in a central passage 128, FIG. 3, of the distal housing part 18. The first part 126 is arranged with a number of cut-outs 130 on opposite sides as well as longitudinally extending ridges 132 on the inner surface that terminate a distance before the end surface of the first part 126.

The activator unit 124 further comprises a second part 134 having a generally disk-shaped body 136 having a diameter that corresponds to the inner diameter of first part 126 and arranged to fit such that a proximal surface of the disk-shaped body 136 is in contact with a distal end surface of the longitudinal ridges 132. The disk-shaped body 136 is further arranged with proximally directed tongues 138, which tongues have a first section 140 generally parallel with the longitudinal direction of the medicament delivery device. The first section 140 is interconnected with an outwardly inclined second section 142. The second section 142 is then interconnected with a third section 144 that is generally parallel with the longitudinal direction.

The second section 142 is arranged with a distally directed ledge 146 that will engage a proximally directed end surface 148 of the cut-out 130 of the first part 126, FIG. 6b, when the two parts are interconnected. Further, the third section 144 will then be placed in the cut-out 130 when interconnected. The free end of the tongue 138 is further arranged with an inwardly directed ledge 150. The disk-shaped body 136 is arranged with two proximally directed arms 152.

The device further comprises a medicament delivery member guard spring 154, coaxially arranged on the actuator sleeve 76. The annular proximal end of the medicament delivery member guard spring 154 is arranged resting on the second annular ring 84 of the actuator sleeve 76, FIGS. 1 and 2, and the annular distal end of the medicament delivery member guard spring 154 is arranged resting on the proximal surface of the stop ledges 102 and 104 of the actuator 90, FIG. 2.

The invention is intended to function as follows. When the power unit 64 is to be assembled, the guide rod 120 is pushed into the actuator 90 from the distal end until the ledges 118 of the guide rod 120 are snapped into the cut-outs 109 of the actuator 90. The actuator sleeve 76 with the medicament delivery member guard spring 154 is pushed onto the actuator 90 until the ledges 102, 104 of the actuator enter the cut-outs 86, 88 of the actuator sleeve 76, preventing further movement. In this position the medicament delivery member guard spring 154 is tensioned and the tongues 94 of the actuator 90 may flex in the generally radial direction. The drive spring 114 is then entered into the plunger rod 112 and the drive spring 114 and plunger rod 112 are pushed into the actuator from the proximal direction, flexing the tongues 94 in the radial direction until the ledges 100 of the tongues 94 enter the annular groove 122, at the same time tensioning the drive spring 114.

The holding element 66 is pushed onto the plunger rod 112 from the proximal direction until the ledges 74 of the holding element 66 also engage with the annular groove 122 of the plunger rod 112 and are positioned radially inwards of the tongues 94 of the actuator 90. Then the actuator sleeve 76 is pushed in the proximal direction onto the actuator 90, thereby preventing the ledges 100 of the tongues 94 of the actuator 90 as well as the ledges 74 of the holding element 66 from escaping the annular groove 122 of the plunger rod 112.

This assembly is then pushed into the distal housing part 18 from the proximal direction and stop when the distally directed stop ledge 102b contacts the central wall 22 as seen in FIG. 2a. The two parts of the activator unit 124 are interconnected and pushed inside the distal housing part from the distal direction. When pushed inside, the ledge 150 of the second part of the activator unit 124 will engage the ledge 108 of the actuator 90 and interconnect the actuator 90 with the activator unit 124, thereby preventing movement of the actuator 90 in the proximal direction. Further, the actuator sleeve 76 is pushed in the proximal direction, but is prevented from movement in the proximal direction due to the ledge 89 on the inner surface of the actuator sleeve 76 abutting the inclined transition surface 96 of the actuator 90 as seen in FIG. 3a.

When the device is to be used, a medicament container 26 is placed in the container holder 52 and the assembly is placed in the proximal housing part 16. The distal housing part 18 with the power unit 64 is then interconnected and locked to the proximal housing part by the attachment elements 20. Further, the inwardly directed ledges 62 at the distal end of the medicament container holder 52 engage with the annular ledge 70 of the holding element 66, interconnecting them. The device is now ready to use. Also the distal part of the medicament delivery member guard 34 will surround the actuator sleeve 76 wherein the inclined tongues 48 will pass the ledge 80 providing a lock in the longitudinal direction of between the medicament delivery member guard 34 and the actuator sleeve 76.

When the medicament delivery device is to be used, the proximal end of the medicament delivery device and thus the medicament delivery member guard 34 is pressed against a dose delivery site. Now the medicament delivery device, apart from the stationary medicament delivery member guard and the inter-connected actuator sleeve 76, is moved in the proximal direction until the distal end of the actuator sleeve 76 comes in contact with the central wall 22 of the distal housing part 18, FIG. 7, wherein the movement is stopped.

Figure 7:
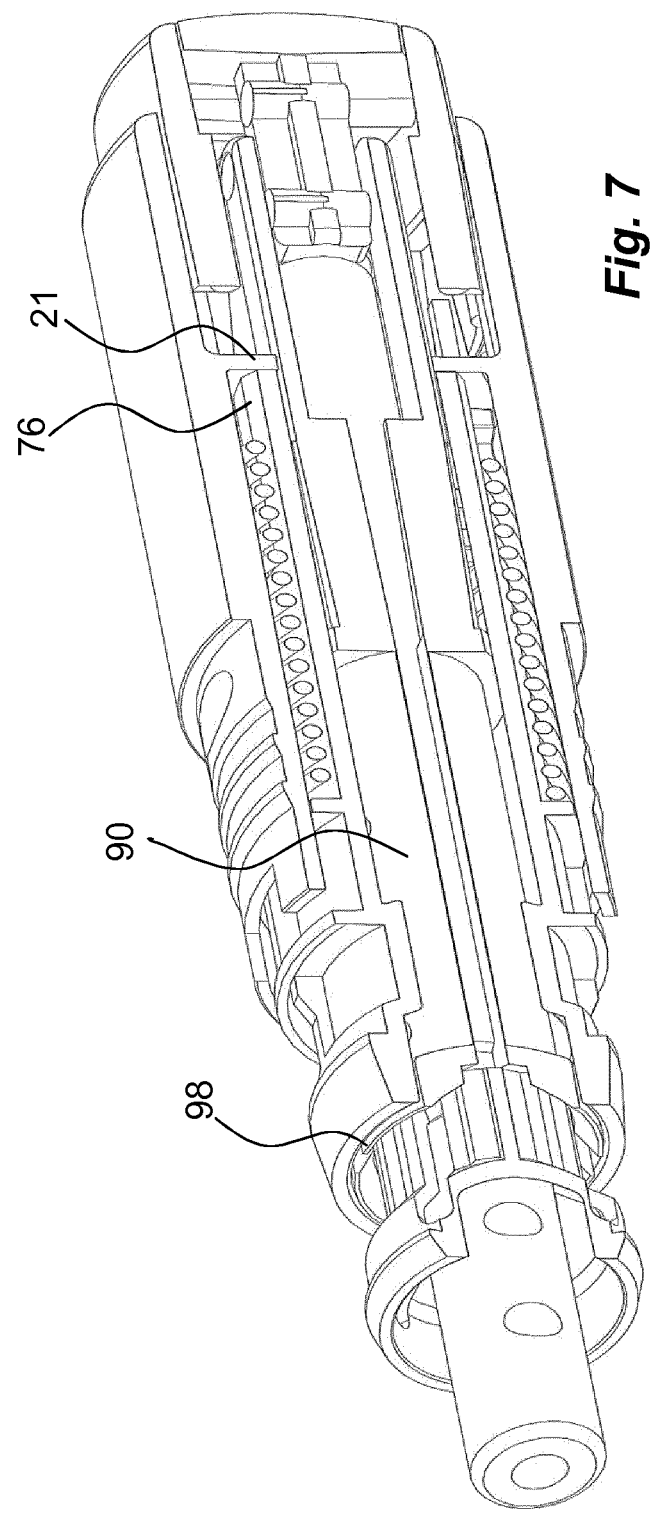
Figure 8A:
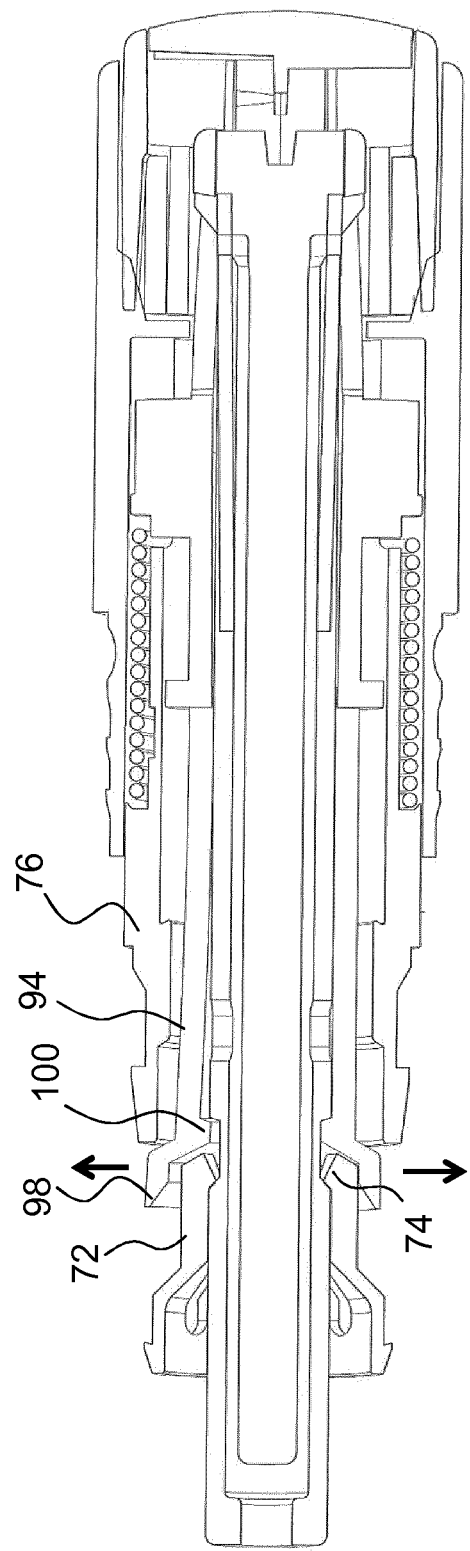
Figure 8B:
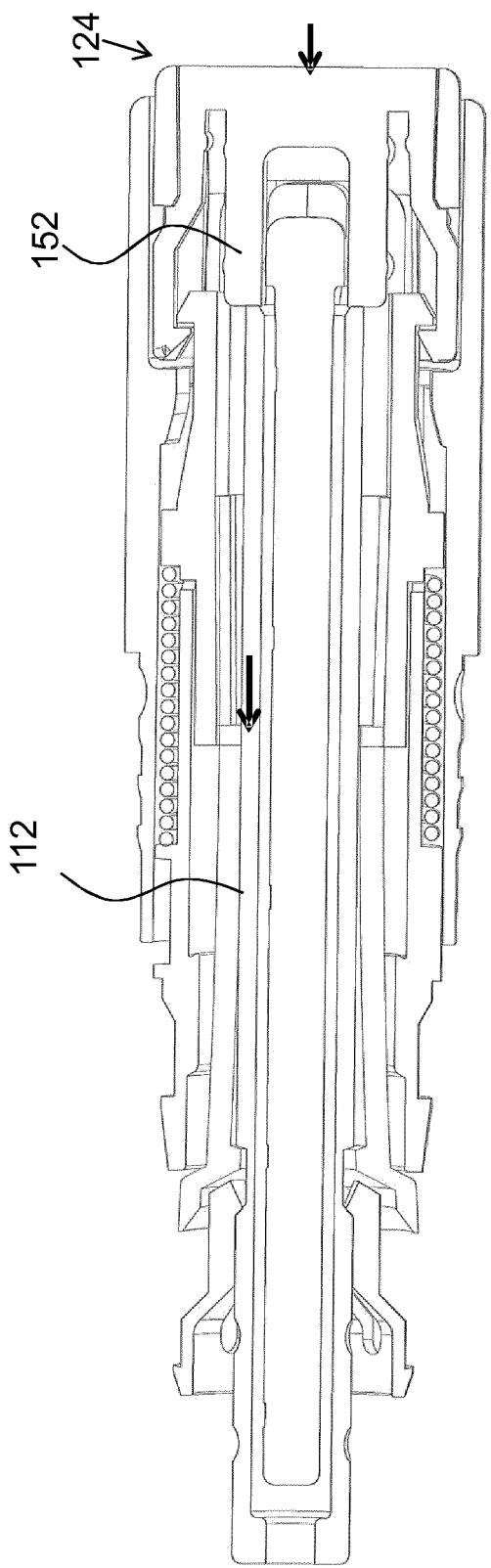

The movement of the actuator 90 in relation to the actuator sleeve 76 has caused the band-shaped part 98 to protrude to some extent out of the proximal end of the actuator sleeve, FIG. 7, setting the power unit in a first activation state. When the user now presses on the activator unit 124 in the proximal direction the proximally directed arms 152 will act on the distal end of the plunger rod 112 and push it in the proximal direction, setting the power unit in the second activation state. Because of the engagement of the actuator 90 with its ledges 100 in the annular groove 122 of the plunger rod 112, also the actuator 90 will move in the proximal direction, FIG. 8b. This movement will cause the band-shaped part 98 to be moved completely out of the actuator sleeve 76, FIG. 8a, and because of the resilient properties of the tongues 94 of the actuator 90, the ledges 100 will move out of the annular groove 122 of the plunger rod 112, thereby releasing the plunger rod 112, which is due to that both activation states have been set.

If for instance the medicament delivery device would be removed from the dose delivery site, than the first activation state is removed. If now the activator unit 124 is pressed, the plunger rod 112 together with the actuator 90 will move proximally in relation to the actuator sleeve 76 to the second activation state, but because the actuator sleeve 76 has not been pushed distally by the medicament delivery member guard 34, the first activation state is not set and the plunger rod 112 will not be released.

Due to the force of the compression spring 114, the plunger rod 112 is urged in the proximal direction. Since the ledges 74 of the holding element 66 is still in the annular groove 122 and the holding element 66 is connected to the medicament container holder 52, the medicament container holder 52 and the medicament container 26 with its medicament delivery member 30 will be moved in the proximal direction, when the plunger rod 112 is moved in the proximal direction, causing a penetration of the medicament delivery member 30 into the tissue of the patient. The movement of the medicament container holder 52 and the medicament container 26 is stopped when the proximally directed surfaces surrounding the neck portion 54 abut the ledge 44 on the inner surface of the medicament delivery member guard 34. It may also be that the force of the compression spring 114 will urge the plunger rod in the proximal direction with such a force that the ledges of the holding element are forced out of the annular groove 122. However, since the plunger rod 112 is acting on the stopper 28 and due to the incompressibility of the medicament inside the medicament container 26 as well as the small passage in the medicament delivery member 30, the medicament container 26 with its container holder 52 will be moved in the proximal direction causing a penetration of the medicament delivery member 30 into the tissue of the patient.

The plunger rod 112 is urged further in the proximal direction wherein the ledges 74 of the holding element 66 will be forced out of engagement with the annular groove 122 due to the flexing properties of the tongues 72 of the holding member. The plunger rod 112 will now act on the stopper 28 inside the medicament container 26, whereby a dose of medicament will be expelled through the medicament delivery member 30. When the plunger rod 112 has come to its most proximal position with the stopper 28 at the proximal end of the medicament container 26, an end-of-dose signal mechanism will be activated in that the distal end of the plunger rod 112 has passed the ledges 100 of the actuator 90, FIG. 9, whereby the tongues 94 of the actuator 90 can flex back radially inwards, which tongues 93 previously have had the additional function of acting as lock/release elements for the actuator 90. Due to the residual force of the drive spring 114, with its distal end acting on the ledges 118 of the guide rod 120, and since the ledges 118 of the guide rod 120 are engaging the actuator 90, the actuator 90 will move suddenly in the distal direction. This will cause the distally directed ledge 102b of the actuator 90 to hit the central wall 22 of the distal housing part 18, producing an audible and tactile signal that the dose delivery sequence is completed.

The user may now remove the medicament delivery device from the dose delivery site. This will cause actuator sleeve 76 and the medicament delivery member guard 34 to be moved in the proximal direction due to the force from the medicament delivery member guard spring 154 acting on the actuator sleeve and because of the connection between the actuator sleeve 76 and the medicament delivery member guard 34, which movement will cause the medicament delivery member 30 to be shielded. In the extended position, the medicament delivery member guard 34 is locked because when the actuator sleeve 76 is moved in the proximal direction by the medicament delivery member guard spring 154, the band-shaped part 98 of the tongues 94 of the actuator 90 will pass the distally directed annular ledge 91 and flex in the radial direction, FIG. 10, whereby the tongues 94 will have the additional function of comprising a medicament delivery guard locking mechanism. This will cause an audible as well as tactile signal that the medicament delivery member guard 34 is locked. Thus, the arms will also have the additional function of acting as a medicament delivery member guard locking signal mechanism. The lock will prevent any attempt to push it in the distal direction due to the band-shaped part 98 abutting the ledge 89. The device is now safe to discard.

It is to be understood that the embodiment described above and shown in the drawings is to be regarded as a non-limiting example of the invention and that it may be modified in many ways within the scope of the patent claims.

COMPONENT LIST 10 medicament delivery device
12 distal end
14 proximal end
16 proximal housing part
18 distal housing part
20 engagement means
22 central wall
23 central passage
24 opening
26 medicament container
28 stopper 30 medicament delivery member
32 central passage
34 medicament delivery member guard
36 proximal part
38 distal part
40 conical part
42 slits
44 ledge
46 opening
48 tongue
50 central opening
52 medicament container holder
54 neck portion
56 guide surface
58 tongue
60 opening
62 ledge
64 power unit
66 holding member
68 body
70 annular ledge
72 tongue
74 ledge
76 actuator sleeve
78 conical part
80 ledge
82 first annular ring
84 second annular ring
86 first cut-out
88 second cut-out
89 ledge
90 actuator
91 ledge
92 cut-out
94 tongue
96 transition surface
98 band-shaped part
100 ledge
102 stop element
104 ledge
106 arm
108 ledge
109 cut-out
110 support surface
112 plunger rod
114 drive spring
116 proximal wall
118 ledge
120 guide rod
122 groove
124 activator unit
126 first part
128 central passage
130 cut-out
132 ridge
134 second part
136 body
138 tongue
140 first section
142 second section
144 third section
146 ledge
148 end surface
150 ledge
152 arm
154 medicament delivery member guard spring

The invention claimed is:

1. A medicament delivery device comprising:
a housing, arranged to accommodate a medicament container;
a power unit arranged inside said housing, said power unit comprising:
a plunger rod,
a drive spring operably arranged to act on the plunger rod and, which is, upon activation, operably arranged to act on said medicament container,
an actuator comprising a plurality of holding elements, capable of releasably holding said plunger rod with said drive spring in a tensioned state, and
an actuator sleeve operably connected to said actuator for releasably locking said plurality of holding elements in a holding state, wherein said plurality of holding elements comprise a plurality of tongues arranged with ledges arranged to engage recesses in said plunger rod;
said medicament delivery device further comprising:
a medicament delivery member guard slidably movable in a distal direction in said housing and arranged to act on said actuator sleeve for moving said actuator sleeve distally in relation to the actuator and for setting said holding elements with said actuator sleeve in a first activation state;
an activator unit comprising push elements arranged to act on an end surface of said plunger rod, wherein said activator unit is slidably movable and arranged to be manually operated in a proximal direction to move said plunger rod and thereby said holding elements proximally for setting said holding elements with said actuator sleeve in a second activation state, and
wherein said plunger rod is released when both activation states are set.

2. The medicament delivery device according to claim 1, further comprising:
a medicament delivery member guard spring arranged to force said medicament delivery member guard in a proximal direction after removal of said medicament delivery device.

3. The medicament delivery device according to claim 1, wherein said plunger rod comprises a hollow plunger rod that defines an internal cavity.

4. The medicament delivery device according to claim 3, wherein said drive spring is arranged inside said internal cavity defined by said hollow plunger rod.

5. The medicament delivery device according to claim 4, further comprising:
a guide rod that extends through the drive spring.

6. The medicament delivery device according to claim 1, further comprising:
a medicament container holder arranged to accommodate the medicament container.

7. The medicament delivery device according to claim 6, wherein said medicament container holder is slidably and coaxially arranged inside said medicament delivery member guard.

8. The medicament delivery device according to claim 7, wherein the medicament container holder comprises a guide surface,
wherein said guide surface is suitable to cooperate with a corresponding shape of an inner surface of the medicament delivery member guard in order to obtain a stop mechanism against rotation of the medicament container holder relative to the medicament delivery member guard.

9. The medicament delivery device according to claim 1, further comprising:
- an end-of-dose signal mechanism, and
- a plurality of lock/release elements arranged to releasably locking said actuator until said plunger rod has reached a proximal end position,
- wherein said plurality of lock/release elements release said actuator,
- whereby said actuator is urged in the distal direction by said drive spring so that said actuator produces an end-of-dose signal.

10. The medicament delivery device according to claim 9,
- wherein said plurality of lock/release elements comprise said holding elements.

11. The medicament delivery device according to claim 10,
- wherein said holding elements are arranged in a locking position by said plunger rod.

12. The medicament delivery device according to claim 11, further comprising:
- a medicament delivery member guard locking signal mechanism,
- wherein said medicament delivery member guard locking mechanism comprises said plurality of tongues interacting with a distally directed ledge on an inner surface of said actuator sleeve such that movement of said medicament delivery member guard in the proximal direction will cause said plurality of tongues to pass said ledge and flex in a generally radial direction, generating a medicament delivery member guard locking signal.

13. The medicament delivery device according to claim 12,
- whereby the engagement of said plurality of tongues with the ledge will lock movement of medicament delivery member guard in the distal direction.

14. The medicament delivery device according to claim 12,
- wherein the medicament delivery member guard locking signal comprises an audible signal.

15. The medicament delivery device according to claim 10, further comprising:
- a medicament delivery member guard locking mechanism,
- wherein said medicament delivery member guard locking mechanism comprises said plurality of tongues interacting with a distally directed ledge on an inner surface of said actuator sleeve such that movement of said medicament delivery member guard in the proximal direction will cause said plurality of tongues to pass said ledge and flex in a generally radial direction,
- whereby the engagement of said plurality of tongues with the ledge will lock movement of medicament delivery member guard.

16. The medicament delivery device according to claim 9,
- wherein said plurality of lock/release elements release said actuator,
- whereby said actuator is urged in the distal direction by said drive spring so that said actuator hits a surface of the housing, producing said end-of-dose signal.

17. The medicament delivery device according to claim 9,
- wherein said end-of-dose signal comprises an audible end-of-dose signal.

* * * * *